United States Patent [19]

Karube et al.

[11] Patent Number: 5,017,494
[45] Date of Patent: * May 21, 1991

[54] BIO-THERMO TIP SENSOR

[75] Inventors: Isao Karube, Tachikawa; Hiroshi Muramatsu, Tokyo, both of Japan

[73] Assignee: Seiko Instruments & Electronics Ltd., Tokyo, Japan

[*] Notice: The portion of the term of this patent subsequent to Apr. 21, 2005 has been disclaimed.

[21] Appl. No.: 847,186

[22] Filed: Apr. 2, 1986

[51] Int. Cl.⁵ .............................................. C12M 1/40
[52] U.S. Cl. .................................... 435/288; 204/403
[58] Field of Search .............. 435/288, 291; 204/403, 204/400, 418

[56] References Cited

U.S. PATENT DOCUMENTS 4,148,305 4/1979 Reichenberger ............... 204/403 X
4,514,276 4/1985 Covington ..................... 204/403 X
4,568,444 2/1986 Nakamura ..................... 204/403 X

OTHER PUBLICATIONS

Mosbach, et al; "Thermal Bioanalyzers in Flow Streams"; *Analytical Chemistry*, vol. 53, No. 1, pp. 83A–94A; Jan. 1981.

*Primary Examiner*—Alan Cohan
*Attorney, Agent, or Firm*—Bruce L. Adams; Van C. Wilks

[57] ABSTRACT

A bio-thermo sensor has an enzyme-modified membrane directly supported on an IC thermal detector in face-to-face contact. The enzyme-modified membrane selectively reacts with a specific chemical substance to generate therein a reaction heat which is converted into an amplified output voltage indicative of the chemical substance by the IC thermal detector. The IC thermal detector includes Darlington-connected transistors which provide high sensitivity and quick response time.

22 Claims, 3 Drawing Sheets

BIO-THERMO TIP SENSOR

BACKGROUND OF THE INVENTION

The present invention relates to the detection of organic compounds in solutions and is widely applicable for chemical and clinical analysis and for monitoring of fermentation processes and waste water treatment. The method of measuring optical absorbance has been, in general, used for detecting organic compounds, but this method requires complicated technical manipulation and long assaying times. Therefore, bio-sensors, which could specifically and rapidly detect organic compounds have recently been developed by using immobilized enzymes and an electrochemical detector. For bio-sensors, the particular electrochemical device that is used for detection is determined by the type of enzyme reaction. This is one of the drawbacks of electrochemical bio-sensors, because they can not use the common electrochemical sensor for various enzyme reactions.

The enzyme thermistor system, which is constructed by using an immobilized enzyme column a, thermistor a, heat-exchanger and a high sensitivity thermostatic bath, has been invented as a multifunction bio-sensor system, for detecting enthalpy change that occurs in all enzyme reactions. Several enzyme thermistor systems have been developed and reported, one of them being reported in the following document: Klaus Mosbach, Bengt Danielsson. Anal. Chem. Vol. 53 No. 1 (1981), Page 83A to 94A.

The thermistor used in the enzyme thermistor system has excellent sensitivity to temperature change, but it has several inherent problems; the characteristics curve between temperature and resistance exhibits poor lineality; selfheating of the thermistors creastes unavoidable experimental error and; for, these reasons, the sensor system must be large.

SUMMARY OF THE INVENTION

It is therefore an object of the present invention to provide an improved bio-sensor having a very small size.

Another object of the invention is to provide an improved bio-sensor having a very short response time.

A further object of the invention is to provide an improved bio-sensor having a good sensitivity.

In accordance with the present invention, the measuring system utilizing a bio-sensor is made simple.

Other objects and advantages of the invention will appear more fully from the following description.

DETAILED DESCRIPTION OF THE INVENTION

Figure 1:
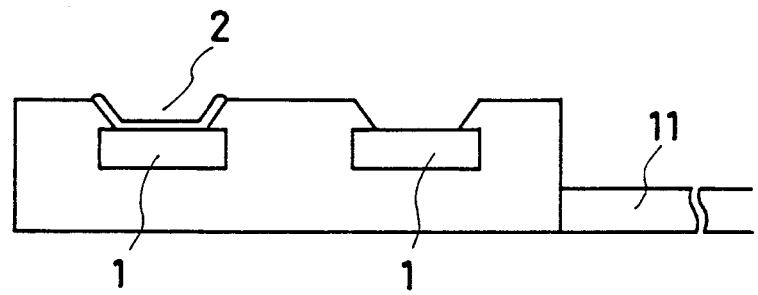
FIG. 1 is a cross sectional diagram of the bio-thermo tip sensor.

A cross sectional diagram of the bio-thermo tip sensor is shown in FIG. 1. The reference numerals 1 and 2 indicate a high sensitive IC thermal sensor or detector configured as a discrete chip and a membrane on which a biocatalyst or enzyme is immobilized, respectively. As shown in FIG. 1, the bio-thermo tip sensor is constructed by using two IC thermal sensors, which are surface coated with an insulating $Si_3N_4$ layer. One of the IC thermal sensor acts as a reference sensor, and the other, which has the enzyme containing membrane 2 fixed onto the surface, of the other IC thermal sensor acts as a detecting sensor. The reference number 11 indicates an electrical connecting wire.

Figure 2:
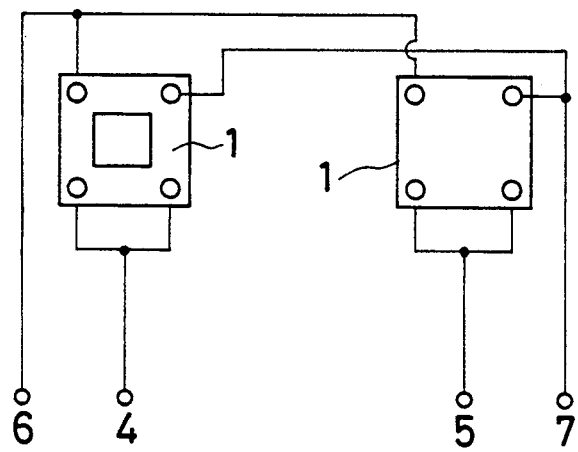
FIG. 2 is the wiring diagram of the bio-thermo tip sensor.

FIG. 2 is the wiring diagram of the bio-thermo tip sensor.

The reference numerals 4, 5, 6 and 7 indicate an output terminal of the detecting sensor, an output terminal of the reference sensor, a GND terminal and a $-3$ V power supply terminal, respectively.

Figure 3:
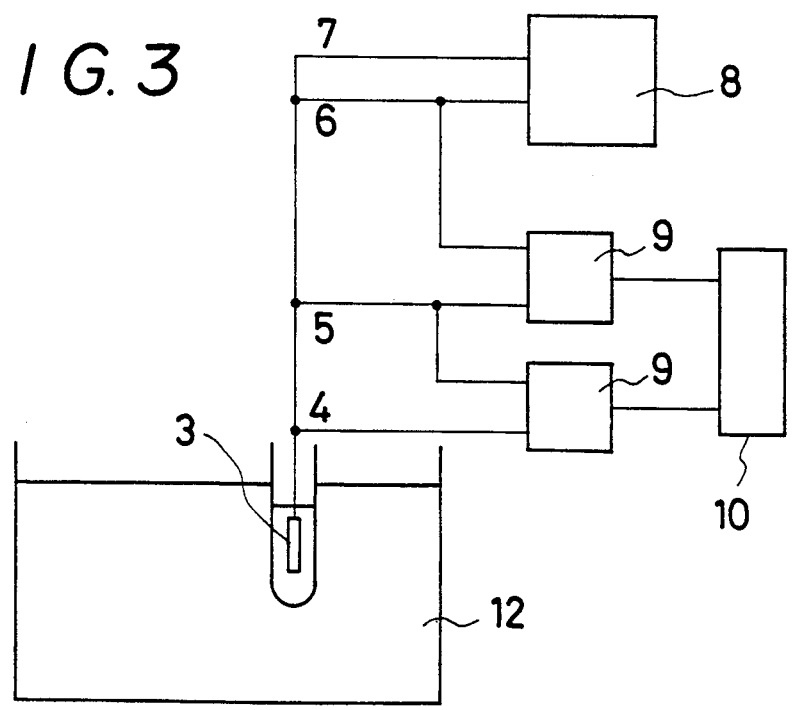
FIG. 3 is a schematic diagram of the measuring system employed for the bio-thermo tip sensor.

FIG. 3 is a schematic diagram of the measuring system employed for the bio-thermo tip sensor.

The measuring system utilizing the bio-thermo tip sensor is provided with a bio-thermo tip sensor 3, a water bath 12, a power supply 8, voltmeters 9 and a computer 12.

Figure 4:
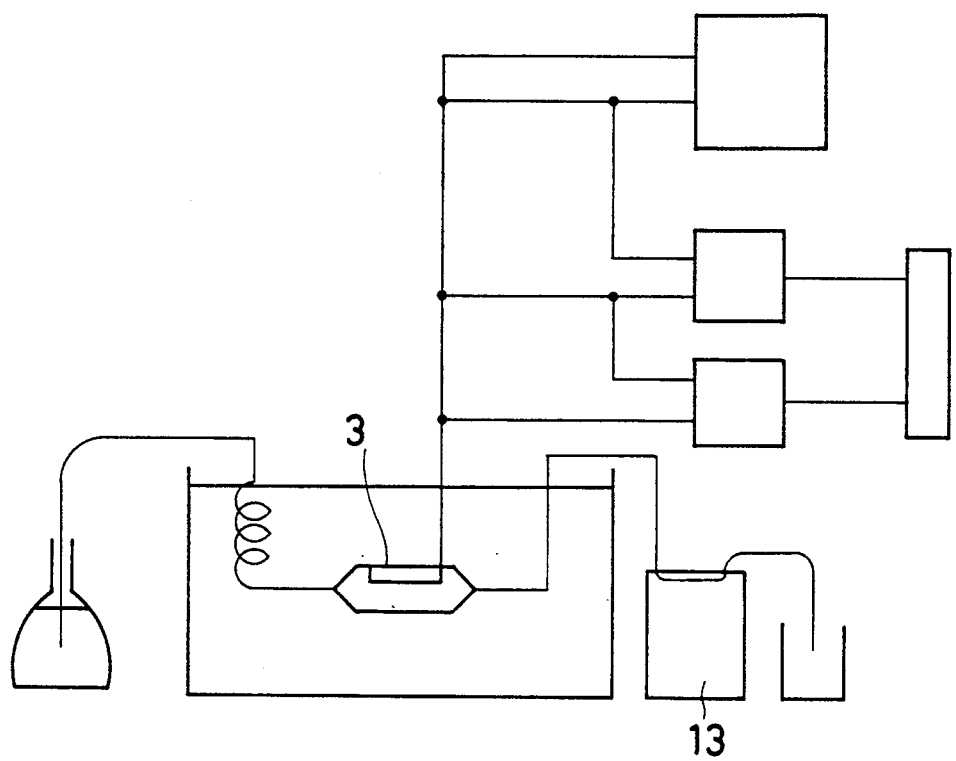
FIG. 4 is a schematic diagram of the flow type measuring system employed for the bio-thermo tip sensor.

The flow type measuring system employed for the bio-thermo tip sensor as shown in FIG. 4 is constructed with a persistent pump, a flow tube, a pool of buffer solution, a sample injection port and the measuring system as shown in FIG. 3.

After the temperature of a thermostatic bath and the output voltage of the IC thermal sensors becomes constant, an aliquot of sample solution is injected into the sensor compartment. The enthalpy change or heat generation due to the bio-catalyst or enzymic reaction is detected by the IC thermal sensor and the level of enthalpy change causes a change in the output voltage of the detecting IC sensor. The difference between the output voltages of the two IC thermal sensors is a measure of the enthalpy change. For batch system analysis, the stationary output voltage change during the reaction is used as a measure of enthalpy change, but for flow system analysis, a peak output voltage change is measured. The output voltage change is easily converted to thermal change, since the IC thermal sensors used in this invention have a characteristic voltage/temperature change of 10 mV/° C.

An explanation referring to a typical example follows;

EXAMPLE

The Glucose-Thermo Tip Sensor

The glucose-thermo tip sensor was constructed by using glucose oxidase as the biocatalyst or enzyme. Two IC thermal sensors were mounted inside a plastic perspex case and encapsulated with insulating epoxy resin except the surface thereof after the electrical connecting wire was attached to the case. The thin membrane used for enzyme immobilization was made by casting a solution of cellose-triacetate (50 mg/ml) dissolved in methylene chloride, 1-8 diamino-4-amino methyl octane (20%) and glutalaldehyde (2%) onto the exposed surfaces of the IC thermal sensors. After 24 hr, this membrane was further treated with glutalaldehyde(2%) for 1 hr and then dipped into glucose oxidase solution (1 mg/ml, pH 7 phoshate buffer, 0.05 M).

The IC thermal sensors used in the present example is as follows: IC thermal sensor includes an integrated circuit constructed by a plurality of transistors connected to form a Darlington connection, wherein a collector of each transistor is connected to a substrate acting as a common collector, the base of a first stage transistor is connected to the substrate and the current source is connected between the common collector and an emitter of final stage transistor.

Figure 5:
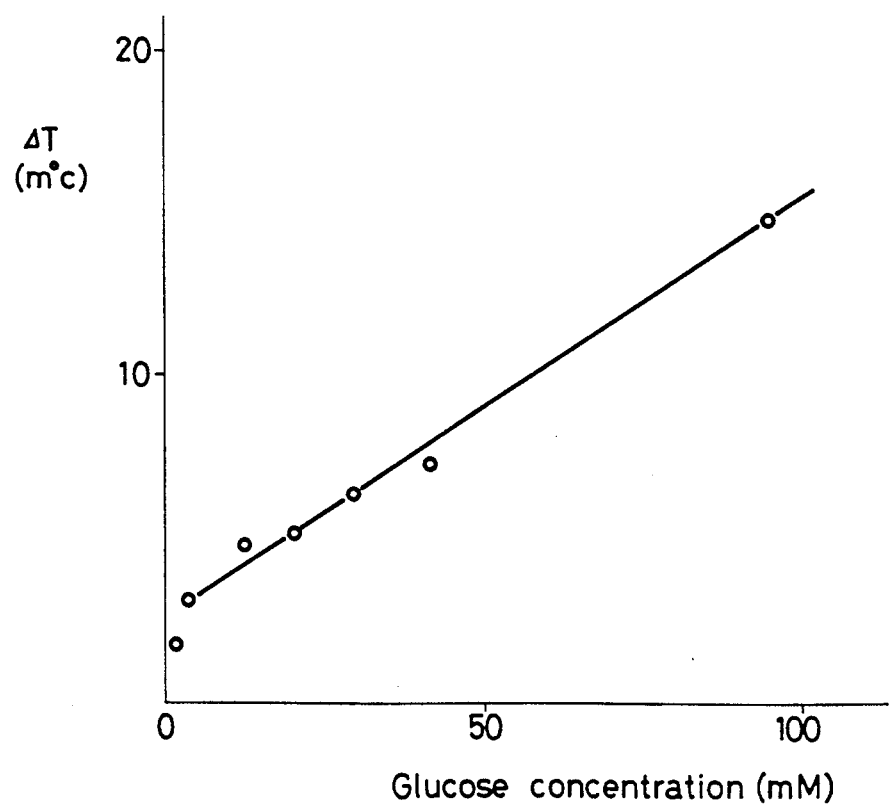
FIG. 5 is the characteristics curve between glucose concentration and thermal change.

The glucose-thermo tip sensor specifically responded to the glucose in a solution. In the batch system, the response of the glucose-thermo tip sensor to glucose concentration was linear in the range of 3-100 mM (FIG. 5). In the flow measuring system, the response of the sensor was reduced, but the measuring time was shorter.

As described above, it is possible to make the bio-thermo tip sensor utilizing high sensitivity IC thermal sensors.

The measuring system is very simple, and only a power supply and a voltmeter is added for measurement, because the high sensitivity IC thermal sensors used in this invention have an internal constant current circuit and a operation amplifier for producing an amplified output voltage. The sensors also have a characteristic of 10 mV/° C. response over a wide temperature range so that a super efficient thermostat bath is not required. The thermal detection circuit of the sensors is situated 3 μm below the thermally sensitive surface so that the thermal detection circuit has a very short response time and good sensitivity better than thermistors. Also, the very small structure of the sensor circuits endears their application to in-vivo analysis.

While the invention has been described with respect to its preferred embodiment, it is to be understood that the words which have been used are words of description rather than limitation and that changes within the purview of the appended claims may be made without departing from the true scope and spirit of the invention in its broader aspects.

What is claimed is:

1. A bio-thermo tip sensor for detecting chemical substances contained in a solution, said sensor comprising:
    (a) a plurality of IC thermal sensors for providing a reference voltage and for converting temperature change to an output voltage relative to the reference voltage;
    (b) wires for connecting said IC thermal sensors to an external power supply and voltmeters;
    (c) electrically inert insulating material for encapsulating said IC thermal sensors and the wires except for the surfaces of detecting parts of said IC thermal sensors; and
    (d) a membrane coated on the surface of at least one of the IC thermal sensors, said membrane having an enzyme immobilized thereon for generating heat when exposed to a solution containing a specific chemical substance to apply the temperature change to the IC thermal sensor.

2. A bio-thermo tip sensor according to claim 1; wherein each IC thermal sensor includes a sensing circuit comprised of Darlington-connected transistors for sensing the temperature change.

3. A bio-thermo tip sensor according to claim 1; wherein the surface of said IC thermal sensor in contact with the solution is covered with a $Si_3N_4$ layer.

4. A bio-thermo tip sensor according to claim 1; including a power supply terminal, a ground terminal and output terminals.

5. A bio-thermo tip sensor according to claim 1; wherein said electrically inert insulating material comprises epoxy resin.

6. A bio-thermo tip sensor according to claim 1; wherein said membrane comprises an organic polymer formed by casting.

7. A bio-thermo tip sensor according to claim 6; wherein said organic polymer comprises cellose triacetate, 1-8 diamino-4-aminomethyloctane and glutaraldehyde.

8. A bio-thermo tip sensor according to claim 1; wherein said immobilized enzyme is covalently coupled to the membrane.

9. A bio-thermo tip sensor according to claim 1; wherein the IC thermal sensors include one IC thermal sensor for providing the reference voltage.

10. A bio-thermal tip sensor according to claim 1; wherein the IC thermal sensors include one IC thermal sensor coated with the membrane.

11. A bio-thermal sensor for detecting chemical substances contained in a sample solution, comprising: a membrane having an enzyme immobilized thereon and operative when exposed to a sample solution for generating heat due to enzymic reaction between the enzyme and a specific chemical substance contained in the sample solution; and an IC thermal detector configured as a discrete chip having a thermally sensitive surface thereon for contactually supporting the membrane on the thermally sensitive surface to directly receive the heat generated in the membrane, the IC thermal detector including an integrated circuit for converting the receive heat into electricity to thereby produce an amplified output voltage indicative of the existence of the specific chemical substance in the sample solution.

12. A sensor according to claim 11; including an additional IC thermal detector disposed adjacent to the first-mentioned IC thermal detector, the additional IC thermal detector having a exposed thermally sensitive surface for producing a reference voltage when exposed to the sample solution.

13. A sensor according to claim 11; wherein the integrated circuit includes means for producing an amplified output voltage proportional to the amount of the received heat.

14. A sensor according to claim 13; wherein the integrated circuit includes means for producing an amplified output voltage linearly proportional to the amount of the received heat to thereby effect quantitative detection of the specific chemical substance.

15. A sensor according to claim 14; wherein the integrated circuit includes Darlington-connected transistors.

16. A sensor according to claim 11; wherein the thermally sensitive surface comprises an outermost layer composed of $Si_3N_4$.

17. A sensor according to claim 11; wherein the membrance comprises an organic polymer.

18. A sensor according to claim 17; wherein the organic polymer comprises cellose triacetate, 1-8 diamino-4-aminomethyloctane and glutanaldeyhde.

19. A sensor according to claim 17; wherein the enzyme comprises an enzyme covalently bonded to the organic polymer.

20. A sensor according to claim 11; wherein the enzyme comprises glucose oxidase specifically reacting on glucose.

21. A sensor according to claim 11; including means for encapsulating the IC thermal detector other than the thermally sensitive surface thereof.

22. A sensor according to claim 21; wherein the means for encapsulating comprises epoxy resin.

* * * * *